US010928391B2

(12) United States Patent
Lin et al.

(10) Patent No.: US 10,928,391 B2
(45) Date of Patent: Feb. 23, 2021

(54) CD318 AS A MARKER FOR, AND CD318 INHIBITION AS A TREATMENT FOR, AUTOIMMUNE DISEASE

(71) Applicants: The Cleveland Clinic Foundation, Cleveland, OH (US); The Regents of the University of Michigan, Ann Arbor, MI (US)

(72) Inventors: Feng Lin, Cleveland, OH (US); David A. Fox, Ann Arbor, MI (US)

(73) Assignees: The Cleveland Clinic Foundation, Cleveland, OH (US); The Regents of the University of Michigan, Ann Arbor, MI (US)

( * ) Notice: Subject to any disclaimer, the term of this patent is extended or adjusted under 35 U.S.C. 154(b) by 148 days.

(21) Appl. No.: 15/997,248

(22) Filed: Jun. 4, 2018

(65) Prior Publication Data

US 2018/0348216 A1  Dec. 6, 2018

Related U.S. Application Data

(60) Provisional application No. 62/515,729, filed on Jun. 6, 2017.

(51) Int. Cl.
| | |
|---|---|
| *G01N 33/564* | (2006.01) |
| *G01N 33/68* | (2006.01) |
| *A61K 39/395* | (2006.01) |
| *C12N 15/113* | (2010.01) |
| *C07K 14/705* | (2006.01) |
| *A61K 47/68* | (2017.01) |

(52) U.S. Cl.
CPC ....... *G01N 33/564* (2013.01); *A61K 39/3955* (2013.01); *C12N 15/113* (2013.01); *G01N 33/6872* (2013.01); *A61K 47/6807* (2017.08); *G01N 2333/70596* (2013.01); *G01N 2800/042* (2013.01); *G01N 2800/065* (2013.01); *G01N 2800/104* (2013.01); *G01N 2800/50* (2013.01)

(58) Field of Classification Search
CPC ............ A61K 38/177; A61K 2039/505; A61K 31/7105; A61K 39/3955; C07K 2317/76; C07K 16/28; C07K 16/2896; C07K 14/705; C07K 14/70596; C12N 15/113; C12N 2310/11; G01N 33/50; G01N 33/53; G01N 33/68; G01N 33/564; G01N 33/6872
See application file for complete search history.

(56) References Cited

U.S. PATENT DOCUMENTS

| | | | | |
|---|---|---|---|---|
| 9,346,886 B2 * | 5/2016 | Auer | ...................... | C07K 16/30 |
| 2007/0031419 A1 * | 2/2007 | Domon | ............ | G01N 33/57438 424/146.1 |
| 2011/0052582 A1 * | 3/2011 | Auer | ...................... | A61P 35/00 424/133.1 |
| 2011/0070246 A1 * | 3/2011 | Bossenmaier | .......... | A61P 35/00 424/174.1 |
| 2011/0091485 A1 * | 4/2011 | Carter | ...................... | A61P 9/00 424/174.1 |

FOREIGN PATENT DOCUMENTS

| | | | |
|---|---|---|---|
| EP | 1396501 A1 * | 8/2003 | |
| WO | WO-2008133851 A1 * | 11/2008 | |

OTHER PUBLICATIONS

Casar et al. Blocking of CDCP1 cleavage in vivo prevents Akt-dependent survival and inhibits metastatic colonization through PARP1-mediated apoptosis of cancer cells. Oncogene 31: 3924-3938, 2012.*
Harrington et al. Cell line and patient-derived xenograft models reveal elevated CDCP1 as a target in high-grade serous ovarian cancer. Brit J Cancer 114: 417-426, 2016.*
He et al. Elevated CDCP1 predicts poor patient outcome and mediates ovarian clear cell carcinoma by promoting tumor spheroid formation, cell migration and chemoresistance. Oncogene 35: 468-478, 2016.*
Iwata et al. CDCP1 identifies a CD146 negative subset of marrow fibroblasts involved with cytokine production. PLOS One 9(10): e109304, 2014 (11 total pages).*
Kollmorgen et al. Antibody mediated CDCP1 degradation as mode of action for cancer targeted therapy. Mol Oncol 7: 1142-1151, 2013.*
Miyazawa et al. CUB domain-containing protein 1, a prognostic factor for human pancreatic cancers, promotes cell migration and extracellular matrix degradation. Cancer Res 70(12): 5136-5146, 2010.*
Nakashima et al. Novel small molecule inhibiting CDCP1-PKCdelta pathway reduces tumor metastasis and proliferation. Cancer Sci 108(5): 1049-1057, 2017.*
Orchard-Webb et al. CUB domain containing protein 1 (CDCP1) modulates adhesion and motility in colon cancer cells. BMC Cancer 14: 754, 2014 (12 total pages).*
Sawada et al. Loss of CDCP1 expression promotes invasiveness and poor prognosis in esophoageal squamous cell carcinoma. Ann Surg Oncol 21: S640-S647, 2014.*
Scherl-Mostageer et al. Identification of a novel gene, CDCP1, overexpressed in human colorectal cancer. Oncogene 20: 4402-4408, 2001.*
Takeda et al. CD318/CUB-domain-containing protein 1 expression on cord blood hematopoietic progenitors. Exp Ther Med 1: 497-501, 2010.*
Wortmann et al. The cell surface glycoprotein CDCP1 in cancer-insights, opportunities, and challenges. IUBMB Life 61(7): 723-730, 2009.*
Yang et al. Dysregulated expression of cell surface glycoprotein CDCP1 in prostate cancer. Oncotarget 6(41): 43743-43758, 2015.*

(Continued)

*Primary Examiner* — Bridget E Bunner
(74) *Attorney, Agent, or Firm* — Casimir Jones, S.C.; Jason R. Bond

(57) ABSTRACT

Provided herein are compositions, systems, kits, and methods for detecting autoimmune disease (e.g., multiple sclerosis and juvenile idiopathic arthritis), and risk of autoimmune disease, in a subject based on the levels of CD318.

5 Claims, 6 Drawing Sheets

Specification includes a Sequence Listing.

(56) References Cited

OTHER PUBLICATIONS

Abdul-Majid et al., Screening of several H-2 congenic mouse strains identified H-2(q) mice as highly susceptible to MOG-induced EAE with minimal adjuvant requirement. Journal of Neuroimmunology. 2000;111(1-2):23-33.
Alonso-Ramirez et al., Rationale for Targeting CD6 as a Treatment for Autoimmune Diseases. Arthritis. 2010;2010:130646.
Aruffo et al., The lymphocyte glycoprotein CD6 contains a repeated domain structure characteristic of a new family of cell surface and secreted proteins. J Exp Med. 1991;174(4):949-52.
Awakura et al., Microarray-based identification of CUB-domain containing protein 1 as a potential prognostic marker in conventional renal cell carcinoma. J Cancer Res Clin Oncol. Dec. 2008;134(12):1363-9.
Bhatt et al., Adhesion signaling by a novel mitotic substrate of src kinases. Oncogene. 2005;24(34):5333-43.
Bott et al., Activation of human T cells through CD6: functional effects of a novel anti-CD6 monoclonal antibody and definition of four epitopes of the CD6 glycoprotein. Int Immunol. 1993;5(7):783-92.
Bowen et al., Cloning, mapping, and characterization of activated leukocyte-cell adhesion molecule (ALCAM), a CD6 ligand. J Exp Med. 1995;181(6):2213-20.
Buhring et al., CDCP1 identifies a broad spectrum of normal and malignant stem/progenitor cell subsets of hematopoietic and nonhematopoietic origin. Stem cells. 2004;22(3):334-43.
Casar et al., In vivo cleaved CDCP1 promotes early tumor dissemination via complexing with activated betal integrin and induction of FAK/PI3K/Akt motility signaling. Oncogene. 2014;33(2):255-68.
Cayrol et al., Activated leukocyte cell adhesion molecule promotes leukocyte trafficking into the central nervous system. Nature immunology. 2008;9(2):137-45.
Chappell et al., Structures of CD6 and Its Ligand CD166 Give Insight into Their Interaction. Structure. 2015;23(8):1426-36.
Conze et al., CDCP1 is a novel marker for hematopoietic stem cells. Ann N Y Acad Sci. May 2003;996:222-6.
De Jager et al., Meta-analysis of genome scans and replication identify CD6, IRF8 and TNFRSF1A as new multiple sclerosis susceptibility loci. Nat Genet. 2009;41(7):776-82.
Dong et al., The cell surface glycoprotein CUB domain-containing protein 1 (CDCP1) contributes to epidermal growth factor receptor-mediated cell migration. J Biol Chem. 2012;287(13):9792-803.
He et al., Elevated CDCP1 predicts poor patient outcome and mediates ovarian clear cell carcinoma by promoting tumor spheroid formation, cell migration and chemoresistance. Oncogene. 2016;35(4):468-78.
He et al., New crossroads for potential therapeutic intervention in cancer—intersections between CDCP1, EGFR family members and downstream signaling pathways. Oncoscience. 2016;3(1):5-8.
Heap et al., Genome-wide analysis of allelic expression imbalance in human primary cells by high-throughput transcriptome resequencing. Hum Mol Genet. 2010;19(1):122-34.
Hooper et al., Subtractive immunization using highly metastatic human tumor cells identifies SIMA135/CDCP1, a 135 kDa cell surface phosphorylated glycoprotein antigen. Oncogene. 2003;22(12):1783-94.
Ikeda et al., Epigenetic regulation of the expression of the novel stem cell marker CDCP1 in cancer cells. J Pathol. 2006;210(1):75-84.
International Multiple Sclerosis Genetics C. The genetic association of variants in CD6, TNFRSF1A and IRF8 to multiple sclerosis: a multicenter case-control study. PLoS One. 2011;6(4):e18813.
Iwata et al., CDCP1 identifies a CD146 negative subset of marrow fibroblasts involved with cytokine production. PLoS One. 2014;9(10):e109304.
Jayaraman, Biocon's first-in-class anti-CD6 mAb reaches the market. Nature biotechnology. 2013;31(12):1062-3.
Joo et al., Evidence for the expression of a second CD6 ligand by synovial fibroblasts. Arthritis Rheum. 2000;43(2):329-35.
Kollmorgen et al., Antibody mediated CDCP1 degradation as mode of action for cancer targeted therapy. Mol Oncol. 2013;7(6):1142-51.
Law et al., Glucocorticoids and histone deacetylase inhibitors cooperate to block the invasiveness of basal-like breast cancer cells through novel mechanisms. Oncogene. 2013;32(10):1316-29.
Lecuyer et al., Dual role of ALCAM in neuroinflammation and blood-brain barrier homeostasis. Proc Natl Acad Sci U S A. Jan. 24, 2017;114(4):E524-E533.
Li et al., Augmenting DAF levels in vivo ameliorates experimental autoimmune encephalomyelitis. Molecular immunology. 2009;46(15):2885-91.
Li et al., CD6 as a potential target for treating multiple sclerosis. Proc Natl Acad Sci U S A. Mar. 7, 2017;114(10):2687-2692.
Lunter et al., Activated leukocyte cell adhesion molecule (ALCAM/CD166/MEMD), a novel actor in invasive growth, controls matrix metalloproteinase activity. Cancer research. 2005;65(19):8801-8.
Miyazawa et al., CUB domain-containing protein 1, a prognostic factor for human pancreatic cancers, promotes cell migration and extracellular matrix degradation. Cancer research. 2010;70(12):5136-46.
Morgan et al., Expression and function of aminopeptidase N/CD13 produced by fibroblast-like synoviocytes in rheumatoid arthritis: role of CD13 in chemotaxis of cytokine-activated T cells independent of enzymatic activity. Arthritis Rheumatol. 2015;67(1):74-85.
Nair et al., CD6 synergistic co-stimulation promoting proinflammatory response is modulated without interfering with the activated leucocyte cell adhesion molecule interaction. Clin Exp Immunol. 2010;162(1):116-30.
Perry et al., Expression of the CUB domain containing protein 1 (CDCP1) gene in colorectal tumour cells. FEBS letters. 2007;581(6):1137-42.
Pinto et al., CD6 as a therapeutic target in autoimmune diseases: successes and challenges. BioDrugs : clinical immunotherapeutics, biopharmaceuticals and gene therapy. 2013;27(3):191-202.
Razorenova et al., VHL loss in renal cell carcinoma leads to up-regulation of CUB domain-containing protein 1 to stimulate PKC{delta}-driven migration. Proc Natl Acad Sci U S A. 2011;108(5):1931-6.
Saifullah et al., Expression and characterization of a novel CD6 ligand in cells derived from joint and epithelial tissues. J Immunol. 2004;173(10):6125-33.
Scherl-Mostageer et al., Identification of a novel gene, CDCP1, overexpressed in human colorectal cancer. Oncogene. 2001;20(32):4402-8.
Seidel et al., Evaluation of CUB-Domain-Containing Protein (CDCP1)-Expression as Predictive Marker of Adhesion-Independant Cell Survival in Breast Cancer Cell Lines. Cancer research. 2009;69(24):878s-s.
Singer et al., CD6 dependent interactions of T cells and keratinocytes: functional evidence for a second CD6 ligand on gamma-interferon activated keratinocytes. Immunology letters. 1997;58(1):9-14.
Spassov et al., Phosphorylation of Trask by Src kinases inhibits integrin clustering and functions in exclusion with focal adhesion signaling. Molecular and cellular biology. 2011;31(4):766-82.
Spassov et al., The structural features of Trask that mediate its anti-adhesive functions. PLoS One. 2011;6(4):e19154.
Spassov et al., The transmembrane src substrate Trask is an epithelial protein that signals during anchorage deprivation. The American journal of pathology. 2009;174(5):1756-65.
Spassov et al., Trask loss enhances tumorigenic growth by liberating integrin signaling and growth factor receptor cross-talk in unanchored cells. Cancer research. 2013;73(3):1168-79.
Swaminathan et al., Validation of the CD6 and TNFRSF1A loci as risk factors for multiple sclerosis in Spain. J Neuroimmunol. 2010;223(1-2):100-3.
Takeda et al., CD318/CUB-domain-containing protein 1 expression on cord blood hematopoietic progenitors. Experimental and therapeutic medicine. 2010;1(3):497-501.

(56) References Cited

OTHER PUBLICATIONS

Uekita et al., CUB-domain-containing protein 1 regulates peritoneal dissemination of gastric scirrhous carcinoma. The American journal of pathology. 2008;172(6):1729-39.
Uekita et al., Roles of CUB domain-containing protein 1 signaling in cancer invasion and metastasis. Cancer science. 2011;102(11):1943-8.
Wong et al., Phosphorylation of the SRC epithelial substrate Trask is tightly regulated in normal epithelia but widespread in many human epithelial cancers. Clinical cancer research: an official journal of the American Association for Cancer Research. 2009;15(7):2311-22.
Wortmann et al., Cellular settings mediating Src Substrate switching between focal adhesion kinase tyrosine 861 and CUB-domain-containing protein 1 (CDCP1) tyrosine 734. J Biol Chem. 2011;286(49):42303-15.
Wortmann et al., The cell surface glycoprotein CDCP1 in cancer—insights, opportunities, and challenges. IUBMB Life. 2009;61(7):723-30.
Wright et al., CDCP1 cleavage is necessary for homodimerization-induced migration of triple-negative breast cancer. Oncogene. 2016, 35(36): 4762-4772.
Zimmerman et al., Long-term engagement of CD6 and ALCAM is essential for T-cell proliferation induced by dendritic cells. Blood. 2006;107(8):3212-20.

\* cited by examiner (A)

(B)

US 10,928,391 B2

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial sequence
<220> FEATURE:
<223> OTHER INFORMATION: Synthetic

<400> SEQUENCE: 1
agacggtggc ggagatcaag                                          20
```

CD318 AS A MARKER FOR, AND CD318 INHIBITION AS A TREATMENT FOR, AUTOIMMUNE DISEASE

The present application claims priority to U.S. Provisional application Ser. No. 62/515,729, filed Jun. 6, 2017, which is herein incorporated by reference in its entirety.

STATEMENT REGARDING FEDERAL FUNDING

This invention was made with government support under EY025373, AR061564, and NS081443 awarded by the National Institutes of Health. The government has certain rights in the invention.

FIELD

Provided herein are compositions, systems, kits, and methods for detecting autoimmune disease (e.g., multiple sclerosis and juvenile idiopathic arthritis), and risk of autoimmune disease, in a subject based on the levels of CD318.

BACKGROUND

Multiple sclerosis (MS) is an inflammatory demyelinating disease of the central nervous system (CNS) that represents a major cause of severe disability in young adults in western countries. Although MS is considered to be an autoimmune disease of unclear aetiology, it is assumed that disease susceptibility is genetically determined while the onset is governed by environmental factors. The polygenic aetiology of MS and its multiple possible interactions with environmental factors determine the phenotypical heterogeneity of the disease, characterized by an enormous variability in the clinical presentation and course of the illness that greatly complicates the physician's ability to diagnose and make prognoses in MS. At the time of its onset, MS can be clinically classified as relapsing-remitting MS (RRMS), in which acute attacks are followed by complete or partial recovery to the pre-existing stage of disability, and primary progressive MS (PPMS), characterized by disease progression from onset, which can occasionally be interrupted by plateaus. Thus, within both RRMS and PPMS clinical phenotypes, stable as well as acute phases of the disease can occur.

SUMMARY

Provided herein are compositions, systems, kits, and methods for detecting autoimmune disease (e.g., multiple sclerosis and juvenile idiopathic arthritis), and risk of autoimmune disease, in a subject based on the levels of CD318.

In some embodiments, provided herein are methods of performing an activity based on a level of CD318 protein or mRNA in a sample from a subject comprising: a) determining protein and/or mRNA expression level of CD318 in a sample from a subject; and b) performing at least one of the following: i) identifying increased protein and/or mRNA expression levels of CD318 in the sample, and treating the subject with a therapeutic agent used to treat an autoimmune disease; ii) generating and/or transmitting a report that indicates the protein and/or mRNA expression levels of CD318 levels are elevated in the sample, and that the subject is in need of a therapeutic agent to treat an autoimmune disease; iii) generating and/or transmitting a report that indicates the protein and/or mRNA expression levels are elevated in the sample, and that the subject has or is at risk of autoimmune disease or complication of an autoimmune disease; iv) characterizing the subject as having an autoimmune disease or having an increased risk for having or developing an autoimmune disease, based on finding elevated levels of the protein and/or mRNA expression levels.

In certain embodiments, provided herein are methods of treatment comprising: a) identifying a subject as having increased expression levels of CD318, and b) treating the subject with a therapeutic agent used to treat an autoimmune disease.

In particular embodiments, provided herein are methods for evaluating the effect of a autoimmune therapeutic agent on a subject comprising: a) determining a first expression level of CD318 in a bodily sample taken from a subject prior to administration of an autoimmune therapeutic agent, and b) determining a second expression level of CD318 in a corresponding bodily fluid taken from the subject following administration of the autoimmune therapeutic agent. In certain embodiments, a decrease in the first level to the second level is indicative of a positive effect of the autoimmune therapeutic agent on autoimmune disease in the subject.

In certain embodiments, provided herein are compositions, systems, or kits comprising: a) a sample comprising synovial fluid or tissue, and b) one or more reagents for detecting CD318 mRNA and/or protein levels in the sample. In further embodiments, the one or more reagents are selected from the group consisting of: anti-CD318 antibodies and nucleic acid probes for detecting CD318 mRNA. In additional embodiments, the sample is from a subject with, or suspected of having, an autoimmune disease.

In some embodiments, the autoimmune disease is selected from the group consisting of inflammatory arthritis, multiple sclerosis and juvenile idiopathic arthritis. In additional embodiments, the autoimmune disease is a non-psoriasis autoimmune disease. In particular embodiments, the autoimmune disease is selected from the group consisting of: Systemic lupus erythematosus (lupus), Inflammatory bowel disease (IBD), Multiple sclerosis (MS), Type 1 diabetes mellitus, Guillain-Barre syndrome, and Chronic inflammatory demyelinating polyneuropathy.

In certain embodiments, the sample is selected from the group consisting of: a plasma sample, a serum sample, synovial fluid sample, and synovial tissue sample. In other embodiments, the determining comprises contacting the sample with an anti-CD318 antibody. In further embodiments, the therapeutic agent used to treat an autoimmune disease is an agent known in the art to treat a particular autoimmune disease (e.g., tocilizumab, rituximab, ofatumumab, belimumab, epratuzumab, abatacept, golimumab, certolizumab, and sifalimumab, Adrecort, Alin, Alin Depot, Decadronal, Dexagrin, Dibasona, Indarzona, Dexamethasone Intensol, DexPak, Taper-Pak, Cortate, and Cortisone Acetate). In particular embodiments, the therapeutic agent used to treat an autoimmune disease is a CD318 inhibitor. In some embodiments, the CD318 inhibitor is selected from an anti-CD318 antibody or antigen binding fragment thereof, anti-CD318 antisense, anti-CD318 small molecule, and anti-CD318 siRNA.

In certain embodiments, the identifying comprises receiving a report that the subject has increased expression levels of CD318 protein and/or mRNA. In other embodiments, the therapeutic agent used to treat an autoimmune disease is an agent known in the art to treat a particular autoimmune disease. In further embodiments, the therapeutic agent used to treat an autoimmune disease is a CD318 inhibitor. In some embodiments, the CD318 inhibitor is selected from an anti-CD318 antibody or antigen binding fragment thereof (e.g., monoclonal antibody or antigen binding fragment thereof), anti-CD318 antisense, anti-CD318 small molecule, and anti-CD318 siRNA.

DEFINITIONS

Figure 1:
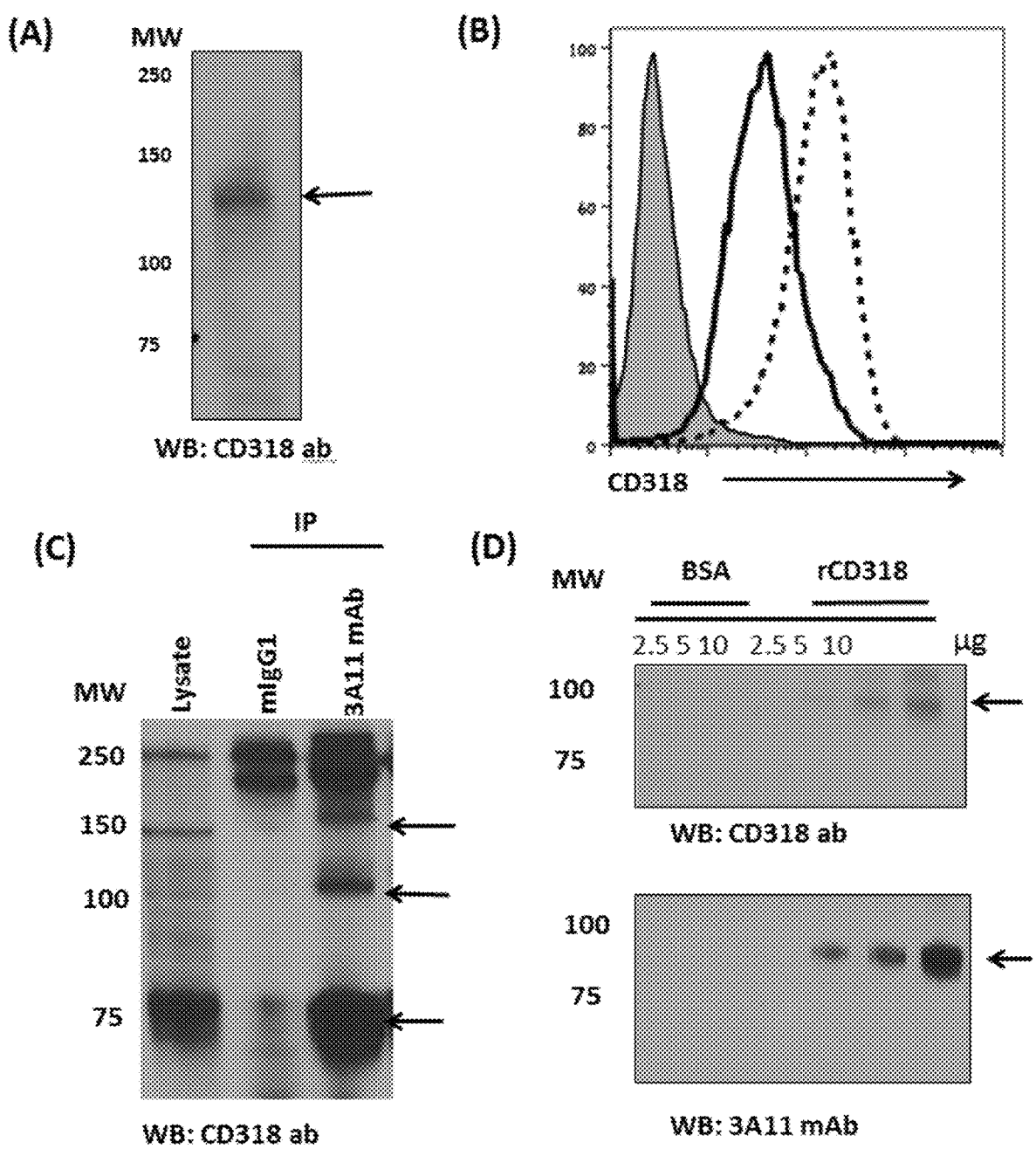
FIGS. 1A-1D CD318 as the potential antigen recognized by mAb 3A11. (Panel A) Probing the HBL-100 cell lysates with a commercial anti-CD318 Ab. Cell lysate were separated by SDS-PAGE and probed with a commercial anti-CD318 Ab in Western Blot, showing a ~135 kDa band (arrow). Data is representative of 2 independent experiments. (Panel B) CD318 upregulation in response to IFNγ stimulation. HBL-100 cells were stimulated with human IFNγ for 72 hr and CD318 expression levels were analyzed by flow cytometry following staining with a commercial anti-CD318 mAb (Clone CUB1). Thin shaded line: isotype control, thick line: without stimulation, dotted line: with stimulation. Data are representative of 3 independent experiments. (Panel C) Probing the mAb 3A11 immunoprecipitates with the anti-CD318 Ab. HBL-100 cell lysates were immunoprecipitated with the same concentrations of mAb 3A11 or mIgG1 control, then the immunoprecipitates were separated by SDS-PAGE and probed with a commercial anti-CD318 Ab. The arrows indicate the full length and different isoforms of CD318 that immunoprecipitated. Data are representative of 2 independent experiments. (Panel D) Three different concentrations (2.5, 5, 10 µg) of rCD318 or BSA control were separated by SDS-PAGE and probed with either mAb 3A11 (Panel D, lower panel) or a commercial anti-CD318 Ab (Panel D, upper panel).

The terms "individual," "host," "subject," and "patient" are used interchangeably herein, and generally refer to a mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos. In some embodiments, the subject is specifically a human subject.

DETAILED DESCRIPTION

Provided herein are compositions, systems, kits, and methods for detecting autoimmune disease (e.g., multiple sclerosis, inflammatory arthritis, and juvenile idiopathic arthritis), and risk of autoimmune disease, in a subject based on the levels of CD318.

CD6 is a marker of T cells and an important T cell regulator (1). Recent genome-wide association studies also identified CD6 as a risk gene for multiple sclerosis (MS) (2-5), an autoimmune disease in which T cells play a vital role in the pathogenesis. CD6 is composed of three extracellular domains (domain 1, 2 and 3), and it functions by interacting with its ligand(s) (6). The domain 3 of CD6 has been shown to be the site that the identified CD6 ligand, CD166, a.k.a., ALCAM (activated leukocyte cell adhesion molecule) binds to (7). However, anti-CD166 antibodies only partially blocked the binding of thymic epithelial cells to CD6 overexpressing COS cells, and mAbs blocking CD6-CD166 interactions do not abolish CD6 function (8, 9). Itolizumab, an anti-CD6 mAb developed in Cuba and approved in India for treating psoriasis, reduces pathogenic T cell responses in patients with psoriasis, but this mAb binds to domain 1 of CD6 instead of domain 3, and it does not interfere with the CD6-CD166 interaction.

Interestingly, UMCD6, a mouse anti-human CD6 mAb that we found highly effective in treating EAE in CD6 humanized mice, also fails to block the CD6-CD166 interaction. All these studies suggest the existence of an additional CD6 ligand, other than CD166, that binds to domain 1 of CD6, and could be critical for CD6 function in autoimmune conditions. Further studies using a CD6 fusion protein as a bait to pull down CD6-binding proteins from synovial fibroblast surface proteins showed the binding of 3 polypeptides (10). One of these polypeptides was identified as CD166 and the identities of other two were unknown (11). A mAb termed 3A11 was developed and the antigen recognized by this mAb was identified as the new ligand of CD6 that binds to its domain 1(11) (12). However, attempts to identify the antigen recognized by mAb 3A11 were not previously successful.

CD318 (a.k.a. CDCP1, TRASK, SIMA135, or gp140) is a cell-surface glycoprotein with an apparent molecular weight of ~140 kDa (13-15). It is composed of 3 extracellular CUB domains, a transmembrane domain, and an intracellular domain. CD318 can be proteolytically cleaved between the two distal CUB domains by certain serine proteases, resulting in different ratios of the ~140 kDa intact molecule and the ~80 kDa cleaved product on different cells. Cleaved CD318 is phosphorylated and activated by Src kinase, then the activated CD318 forms a complex with activated 131 integrin and activates FAK/PI3K/Akt motility signaling to promote early tumor dissemination (16). Under normal conditions, CD318 is present on many epithelial cells, (17) some hematopoietic cells, (18) and mesenchymal stem cells (19). CD318 is also present on many tumor cells (20). Upregulation of CD318 expression is associated with a poor prognosis for many cancer patients (14, 21-25). Interestingly, a recent study using CD318 KO mice showed that two different oncogene-driven tumors grow much faster in CD318 KO mice than in wild-type (WT) control mice. (26) Lack of CD318 in these mice enhances tumor growth potentially by liberating integrin signaling and growth factor receptor cross-talk in unanchored tumor cells. (26) So far, all studies on CD318 have been limited to its direct signaling effect in tumor cells, and its possible role in regulating immune responses has never been examined.

In work conducted during development of embodiments of the present disclosure, using mass spectrum techniques, we identified the antigen recognized by mAb 3A11 as CD318. To validate the proteomics results, we probed proteins immunoprecipitated by mAb 3A11 using established anti-CD318 antibodies and probed recombinant CD318 protein by mAb 3A11 in Western Blots. We also compared staining patterns of both mAb 3A11 and established anti-CD318 mAbs using cells that are known to be positive or negative for CD318, and engineered cells with upregulated or downregulated levels of CD318. In addition, we confirmed the binding of CD318 to CD6 by using soluble CD6 protein as a bait in pull-down assays and by staining WT and CD166 deficient cells with the soluble CD6 followed by flow cytometric analyses. We immunized the CD318 KO mice to induce experimental autoimmune encephalomyelitis (EAE), and found that CD318 KO mice show ameliorated central nervous system (CNS) injury in association with reduced pathogenic T cell responses and infiltration into the CNS. Finally, we examined CD318 expression on synovial fibroblasts from rheumatoid arthritis (RA) patients, measured levels of soluble CD318 in synovial fluids from arthritis patients, and studied its potential roles in recruitment and retention of T cells in synovial tissue. These results showed that CD318 is the new CD6 ligand recognized by mAb 3A11, and indicate that CD318 could be a new biomarker and target for the diagnosis and/or treatment of autoimmune diseases such as MS and inflammatory arthritis.

EXAMPLES

The following examples are illustrative and not intended to limit the scope of the present invention.

Example 1

It has been speculated that CD6, an important regulator of T cells, functions by interacting with its currently identified ligand, CD166, but treatment studies suggest that the CD6-CD166 interaction might not account for important functions of CD6 in autoimmune diseases. The antigen recognized by mAb 3A11 has been proposed as a new CD6 ligand distinct from CD166, yet the identity of it is hitherto unknown. In this Example, we have identified this new CD6 ligand as CD318, a cell surface protein previously found to be present on various epithelial cells and many tumor cells. We found that like CD6 knockout (KO) mice, CD318 KO mice are also protected in experimental autoimmune encephalomyelitis. In humans, we found that CD318 is highly expressed in synovial tissues, and participates in CD6-dependent adhesion of T cells to synovial fibroblasts. In addition, soluble CD318 is chemoattractive to T cells and levels of soluble CD318 are selectively and significantly elevated in the synovial fluid from patients with rheumatoid arthritis and juvenile inflammatory arthritis. These results establish CD318 as a new ligand of CD6, and a new biomarker and/or target for the diagnosis and treatment of autoimmune diseases such as multiple sclerosis and inflammatory arthritis.

Methods and Reagents
Animals

Wild-type (WT) and CD318 KO mice (C57BL/6 background) were ordered from Jackson Laboratory and maintained under pathogen-free conditions in the animal facility of Lerner Research Institute, Cleveland Clinic.

Cell Culture

The HBL-100, Raji, A549, Molt4 and MCF, wild type (WT) HT-1080 and CD166 knockout (KO) cell lines were cultured in RPMI supplemented with 10% FBS, L-glutamine, penicillin/streptomycin and Na-pyruvate. WT MDA-468, and CD318 knockdown cell lines as well as transfected CHO cells expressing human CD6 on their surface (6) were cultured in DMEM supplemented with 10% FBS, L-glutamine, penicillin/streptomycin, Na-pyruvate and 300 µg/ml of G418. MDA-468 expressing empty vector or doxycycline-inducible CD318 were also cultured in the same media described above with Zeocin in place of G418. Caco-2 cells were also cultured in the same media described in the absence of selection pressure. MDA-468 expressing vector control and doxycycline-inducible CDCP1 were stimulated with 100 ng/ml of doxycycline overnight (32).

CD166 Knockout Cell Line Development

CD166 was knocked out in the HT-1080 cells using CRISPR/Cas 9 technology. In brief, RNA (AGACGGTGGCGGAGATCAAG, SEQ ID NO: 1, Horizon Discovery, UK) was transfected into cells by lipofection. Transfection efficiency above 20% is considered successful. Efficiency was monitored by the surrogate mSarker, GFP. Cells lacking cell-surface CD166 were selected by fluorescence-activated cell sorting using an antibody against the extracellular domain of CD166 (R&D Systems, MAB656). Cell population was further purified by single-cell colony formation in soft agar. After identification of pure, CD166-negative clonal populations, 5 clones were selected at random and mixed to create the CD166-KO cell line.

Antibodies

3A11 mAb was previously developed and characterized (11) (10). mAbs against human CD166, human CD318 (clone: CUB1) and mouse IgG2b isotype control were all obtained from (Biolegend, San Diego, Calif.). The polyclonal anti-CD318 antibody was obtained from Thermo Scientific, (Waltham, Mass.). Recombinant human CD6 was obtained from R&D, (Minneapolis, Minn.). Recombinant mouse CD6 was described previously (10). Purified human IgG1 was obtained from Sigma-Aldrich, (St. Louis, Mo.). Alexa 488-conjugated donkey anti-mouse IgG and Alexa 488-conjugated donkey anti-human IgG were both obtained from ImmunoResearch, (West Grove, Pa.). Alexa 488-conjugated polyclonal anti-human CD6 was obtained from R&D, (Minneapolis, Minn.). FITC-conjugated mouse IgG isotype control was obtained from Biolegend, (San Diego, Calif.).

Immunoprecipitations
3A11 mAb IP:

HBL-100 breast carcinoma cells were biotinylated using E-Z link sulfo-NHS-LC biotin and subsequently lysed in NP-40 lysis buffer (Invitrogen, Carlsbad, Calif., USA) containing 0.1% SDS (Fisher Scientific, Waltham, Mass.), 0.1% deoxycholic acid (Sigma-Aldrich, St. Louis, Mo., USA) and one complete tablet of protease inhibitor (Roche, Mannhein, Germany) on ice for 30 min. Immunoprecipitation was performed overnight at 4° C. using either mouse IgG1 or 3A11 mAb. Antigen-antibody complexes were pulled down using protein (A+G). Following antigen-recombinant protein complex pull down, the samples were boiled for 5 min in 2× Laemmli sample buffer (Bio-Rad, Hercules, Calif.). For Western Blot: samples were loaded onto an SDS-PAGE and following electrophoresis, proteins were transferred to a polyvinylidene difluoride (PVDF) membrane for western blotting. The membrane was incubated for 1 hour at room temperature with blocking buffer containing 5% BSA and 0.05% Tween 20. Following blocking, the protein was detected using streptavidin-HRP conjugate and visualized using the chemiluminescent substrate ECL (Amersham Biosciences, Buckinghamshire, U.K.). In some experiments, HBL-100 carcinoma cells were not biotinylated prior to the preparation of cell lysates for immunoprecipitation with either mouse IgG1 or 3A11 mAb as described above. Following blocking of the PVDF membrane, the membrane was incubated with CDCP1 (Thermo Scientific, Waltham, Mass.) primary antibody and followed by HRP-conjugated goat anti-rabbit (Southern biotech, Birmingham, Ala.). The protein was visualized using ECL Western Blot detection reagent (Amersham Biosciences, Buckinghamshire, U.K.).

Recombinant Soluble CD6 IP:

HT1080 CD166-KO cells were lysed in 0.5% NP-40 (Roche, Mannhein, Germany) lysis buffer on ice for 30 min. Lysates were immunoprecipitated with either purified human IgG1 or recombinant mouse CD6 overnight at overnight at 4° C. Protein A/G-agarose beads was then added to the samples for 3 hr. Following antigen-recombinant protein complex pull down, the samples were boiled for 5 min in 2× lamini sample buffer (Bio-rad, Hercules, Calif.). For Western Blot: samples were loaded onto an SDS-PAGE and following electrophoresis, proteins were transferred to a PVDF membrane for Western Blotting. Following blocking of the PVDF membrane, the membrane was incubated with an anti-CDCP1 (Thermo Scientific, Waltham, Mass.) primary antibody and followed by HRP-conjugated goat anti-rabbit IgGs (Southern biotech, Birmingham, Ala.).

In-Gel Digestions and Mass Spectrometry

Proteins immunoprecipitated by mAb 3A11 were separated by SDS-PAGE. Bands at the appropriate size were excised and destained with 50% acetonitrile in 100 mM ammonium bicarbonate followed by 100% acetonitrile. Cysteine residues were first reduced by incubating the sample with 20 mM DTT at room temperature for 60 min, and then alkylated with 50 mM iodoacetamide for 30 min in the dark. The gel pieces were washed with 100 mM ammonium bicarbonate, dehydrated in acetonitrile, dried in a SpeedVac centrifuge, and then rehydrated in 50 mM ammonium bicarbonate containing sequencing grade modified trypsin for overnight digestion at 37° C. The resulting proteolytic peptides were extracted from the gel with 50% acetonitrile in 5% formic acid, dried and reconstituted in 0.1% formic acid for LC-MS/MS analysis.

The digests were analyzed by LC-MS/MS using Orbitrap Elite Hybrid Mass Spectrometer (Thermo Electron, San Jose, Calif.), equipped with a Waters nanoAcquity UPLC system (Waters, Taunton, Mass.). The spectra were acquired in the positive ionization mode by data-dependent methods consisting of a full MS scan at 120,000 resolution and MS/MS scans of the twenty most abundant precursor ions in ions trap by collision-induced dissociation at normalized collision energy of 35%. A dynamic exclusion function was applied with a repeat count of 2, repeat duration of 30 s, exclusion duration of 45 s, and exclusion size list of 500. The obtained data were submitted for a database search using Mascot Daemon (Matrix Science, Boston, Mass.). Carbamidomethylation of Cys was set as a fixed modification, whereas oxidation of Met was selected as variable modifications. The mass tolerance was set as 10 ppm for precursor ions and 0.8 Da for productions. SwissProt (July, 2014) database (546000 sequences; 194259968 residues) was used for searching against the taxonomy of human (20210 sequences). The significance threshold p-value was set to <0.05. Proteins hits with at least two unique peptides at Mascot score >20 were considered to be identified.

Flow Cytometric Staining

For CD318, CD166 and 3A11 mAb cell surface staining, cells were stained with anti-human CD318, anti-human CD166, and 3A11 mAb respectively on ice for 30 min. Following 3A11 mAb cell surface staining cells, these cells were washed and subsequently stained with the secondary antibody Alexa 488-conjugated donkey anti-mouse IgG and analyzed by flow cytometry. For soluble CD6 cell surface staining, HT1080 CD166-KO cells were incubated with 1 µM recombinant human CD6-Ig or human IgG1 at 4° C. for 45 min. After 45 min, the cells were washed and subsequently stained with Alexa 488-conjugated donkey anti-human IgG at 4° C. for 30 min, washed and analyzed by flow cytometry. In some experiments, HBL-100 cells or synovial fibroblasts were stimulated with 1000 U/ml of human IFN-γ for 72 hr prior to analyzing the expression of CD318 by flow cytometry. For rCD318 binding to control or human CD6-expressing CHO cells, these cells were incubated with rCD318 at 4° C. for 45 min. After 45 min, the cells were washed and subsequently stained with PE-conjugated mAb against human CD318 at 4° C. for 30 min, washed and analyzed by flow cytometry.

Production of Recombinant CD318 Extracellular Domains and Western Blots:

Gene sequence encoding for the extracellular domains of CD318 with a C-terminal 6×His-tag, was synthesized (Genscript, NJ) and cloned into the expression vector pcDNA3.1. After transfection of the expression construct into 293 cells for transient expression, recombinant CD318 in the culture supernatant was purified by nickel affinity chromatography following published protocols. For western blots, the same amount of either recombinant CD318 or BSA was separated by SDS-PAGE and transferred to a PVDF membrane, then probed with either the 3A11 mAb or a rabbit anti-human CD318 antibody, followed by either rat anti-mouse HRP conjugate or goat anti-rabbit HRP conjugate respectively. Protein bands were visualized using the chemiluminescent substrate ECL.

Induction of EAE

EAE was induced by active immunization, and disease severity was assessed by assigning clinical scores following previously published protocols (51, 52). In brief, 8-10 week old female mice were immunized at the base of the tail and in both thighs with 200 µg of mouse $MOG_{35-55}$ peptide (custom synthesized by GenScript USA Inc., Piscataway, N.J.) emulsified in Complete Freund's Adjuvant (CFA) (Difco Laboratories, Inc., Detroit, Mich.) that had been supplemented with *Mycobacterium tuberculosis* strain H37Ra to 4 mg/ml. 0.2 µg of Pertussis toxin (List Biologic Laboratories, Inc., Campbell, Calif., USA) was injected i.p. immediately after immunization and the following day. Clinical severity was assessed daily with a 0 to 5 scoring system (0, no signs; 1, flaccid tail; 2, impaired righting reflex and/or gait; 3, partial hind limb paralysis; 4, total hind limb paralysis; 5, moribund or dead).

Histological Analysis of Spinal Cords

Following sacrifice of the mice, spinal cords were removed and fixed in 10% Formalin in PBS buffer for 24 h, then embedded in paraffin. Sections were cut at 5 µm on a microtome and stained with hematoxylin and eosin (H&E) to assess CNS inflammatory infiltrates following established protocols.

Analysis of CD4+ T Cell Infiltration in the Spinal Cord of EAE Mice

At the end of EAE experiments, mice were perfused through the left ventricle using 100 ml of HBSS, then spinal cords were dissected, washed by HBSS, and digested with 10 mg/ml collagenase d (Roche, Basel, Switzerland) at 37° C. for 45 min with shaking every 15 minutes. Cells released from the digestion were passed through a 70-µm cell strainer and separated by using 38% Percoll. After this, single cell suspension was prepared and stained with an anti-CD4 mAb (Biolegend, San Diego, Calif.) followed by flow cytometric analysis.

Th1 and Th17 Recall Assays

Splenocytes were collected immediately following sacrifice of the mice. After lysing the red blood cells, $0.4 \times 10^6$ splenocytes were incubated with or without 10 µg/ml of the $MOG_{35-55}$ peptide in 100 µl of RPMI medium with 10% FBS in each well of a 96 well plate. After 72 hrs, IFN-γ and IL-17a levels in the culture supernatants were measured by respective ELISA (Biolegend, San Diego, Calif.) following manufacturer-provided protocols.

Analysis of CD318 Expression on BMECs.

Mouse BMEC were isolated following a published protocol (Ruck T, Bittner S, Epping L, Herrmann A M, Meuth S G. Isolation of primary murine brain microvascular endothelial cells. J Vis Exp 2014: e52204). In brief, mouse brains were isolated, and the brain stems, cerebella, thalami, and meninges were removed under a dissecting microscope. The remaining tissue was minced and digested by 5 mg/ml collagenase CLS2 (Worthington Biochemical Corp. Lakewood, N.J.) in DMEM for 1 hr at 37° C., then washed with 20% BSA-DMEM and centrifuged at 1,000×g for 20 min at 4° C. The pellet was re-suspended in 1 mg/ml collagenase/ dispase (Worthington Biochemical Corp. Lakewood, N.J.) and incubated for another 1 hr at 37° C. After the final washing, the resultant cells were cultured in endothelial cell medium (PeproTech, Rocky Hill, N.J.). The isolated BMEC purity was determined by flow cytometric analysis after staining the cells with an anti-CD34 mAb (Biolegend, CA). For CD318 expression detection, the cells were incubated with 10 μg/ml sheep anti-mouse IgG (R&D Systems) or sheep IgGs, then analyzed by a flow cytometer.

Synovial Tissue and Synovial Fluid Specimens:

Synovial tissue specimens were obtained from patients with rheumatoid arthritis (RA, n=13) and osteoarthritis (OA, n=20) at the time of arthroplasty. Normal synovial tissues were obtained from cadavers (n=17). A portion of each tissue was homogenized for ELISA assays. Synovial fluids were obtained at therapeutic arthrocentesis from patients with RA (n=36), OA (n=28) and juvenile inflammatory arthritis (JIA, n=10). In all cases, synovial tissue and fluid specimens were excess materials obtained at procedures performed for clinical indications.

Immunohistochemistry (IHC) Staining:

Human ST sections were fixed in cold acetone and then treated with 3% peroxidase in 0.1M Tris. Tissues were blocked with 3% horse serum. The sections were incubated with the 3A11 mAb (mouse anti-human CD318 IgG) or purified mouse IgG (MyBioSource, San Diego, Calif.) for an additional hour. Then a 1:100 dilution of horse anti-mouse biotinylated secondary antibody (Vector), was added to the tissue sections and incubated at room temperature. Then VECTASTAIN Elite ABC HRP Kit (Vector, Olean, N.Y.) was added at a 1:10,000 dilution. Finally, diaminobenzidine tetrahydrochloride substrate (DAB) (Vector) was added to the sections. The sections were then counterstained with Harris' hematoxylin, and dipped in saturated lithium carbonate solution for bluing and then mounted with cover slips.

Enzyme-Linked immunosorbent Assay (ELISA):

Levels of soluble CD318 in sera and synovial fluids were measured by an ELISA kit (R&D Systems, MN) per the manufacturer's protocol.

T-Cell Chemotaxis Assay.

CD3+ T-cells were isolated using a RosetteSep lymphocyte isolation kit (Stem Cell Technologies, Danvers, Mass.) and instructions were followed per the manufacturer's protocol. Cytospin examination was performed to ensure that the isolated cells were lymphocytes. Chemotaxis membranes were coated with type IV collagen (Sigma-Aldrich, St. Louis, Mo.) used at 1 ug/ml overnight and dried. 40 ul of varying concentrations of CD318 (100, 200, 400, 800, and 1600 pg/ml) were added to wells in the bottom of the chamber. T-cells ($1.0 \times 10^6$ cells/ml in PBS) were placed in the top wells of a 48-well Boyden chemotaxis chamber. PBS served as the negative control in this experiment. After 18 hours, the membranes were then removed and stained with Diff-Quik (Thermo Fisher Scientific, Kalamazoo, Mich.). Readings represent the number of cells migrating through the membrane (the sum of three high power 40× fields/well, averaged for each quadruplicate well).

Adhesion Assay:

CD3+ T-cells were isolated using a RosetteSep lymphocyte isolation kit (Stem Cell Technologies) and were stained with carboxyfluorescein succinimidyl ester (CFSE) (Thermo Fisher Scientific, Waltham, Mass.) at 5 uM. RA synovial fibroblasts at culture passage 4-8 were stimulated with 1000 U/mL IFN-$^\gamma$ (Cell Signaling Technologies, Danvers, Mass.) in 10% FBS in culture media or in 10% FBS for 3 days. Fibroblasts were then incubated with mouse IgG, anti-CD318, anti-CD166, or both anti-CD318 and anti-CD166. T-cells were added at 50,000 cells per well onto fibroblasts and incubated for 1 hour at room temperature. Intensity was measured with a Synergy plate reader.

Statistics

EAE clinical scores were evaluated with two-way ANOVA and Bonferroni's post-testing. One-tailed p-values <0.05 were considered significant. MOG recall T cell assays were evaluated with nonparametric t Test. One-tailed p-values <0.05 were considered significant.

Study Approval and Animal Use.

All procedures involving mice were approved by the Institutional Animal Care and Use Committee of Cleveland Clinic, and all were done in accordance with the U.S. Department of Health and Human Services Guide for the Care and Use of Laboratory Animals, and institutional guidelines. Human tissues samples were collected as part of study number 2002-0875, which was approved by the University Michigan IRB. All subjects provided informed consent prior to their participation in the study.

Results

Identification of the Antigen Recognized by mAb 3A11:

It had been previously established that mAb 3A11 recognizes an uncharacterized CD6 ligand that binds to domain 1 of CD6 (11), the same domain that Itolizumab, the anti-CD6 mAb approved for treating psoriasis in India (27) binds to, suggesting that this new CD6 ligand might be more important than the already identified CD6 ligand, CD166, for CD6 function in disease. To determine the identity of the antigen recognized by mAb 3A11, we investigated HBL-100 cell surface proteins pulled down by this mAb by mass spectrum (MS) analysis. We found that CD318-related peptides were abundant in the mAb 3A11 precipitates, indicating that the protein recognized by 3A11 could be CD318. We then probed whole HBL-100 cell lysate with an anti-CD318 Ab in western blot and assessed CD318 expression levels on HBL-100 cells by flow cytometry before and after IFNγ stimulation. We found that CD318 met the previously established characteristics of the potential mAb 3A11 antigen candidate (11) such as 1) it has a molecular weight of ~130 kDa (FIG. 1A), and 2) its expression can be upregulated by IFNγ stimulation (FIG. 1B).

Western Blots Using a Commercial Anti-CD318 Antibody and Recombinant CD318:

To validate the MS results, we performed western blotting of the above immunoprecipitates using a commercial anti-CD318 antibody (Pierce, Ill.) and found that these antibodies detected three bands (FIG. 1C), including a ~140 kDa band and a ~80 kDa band, in the mAb 3A11 immunoprecipitates, but not the control IgG1 immunoprecipitates. In addition, we prepared recombinant soluble CD318 (rCD318) by synthesizing an artificial gene coding for the extracellular domains of CD318 with a C-terminal 6×His-tag, and cloned it into the expression vector pcDNA3.1. After transfecting the expression construct into 293 cells, we purified the rCD318 in the culture supernatants by nickel affinity chromatography following published protocols (13), and verified the protein by western blot using an anti-His tag antibody. We then probed the rCD318 and the same amount of BSA with mAb 3A11 or an established anti-CD318 antibody in western blots, and found that both the mAb 3A11 and the anti-CD318 antibody selectively recognized rCD318 but not the BSA (FIG. 1D).

Figure 2:
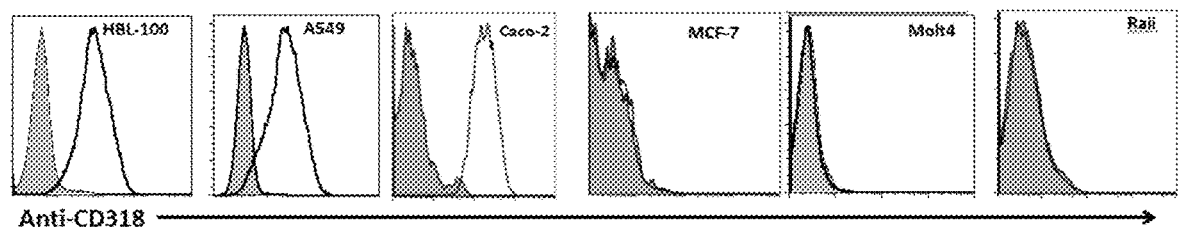
FIGS. 2A-2B The anti-CD318 mAb and mAb 3A11 have an identical staining pattern on cells previously known to express or lack CD318 expression on the cell surface. Reported CD318-positive cells (HBL-100, A549 and Caco-2) and negative cells (MCF-7, Molt-4 and Raji) were stained either with the anti-CD318 mAb (Panel A) or mAb 3A11 (Panel B) and analyzed by flow cytometry. Data are representative of three independent experiments. Shaded histogram: isotype controls (mIgG2b for CD318 staining and mIgG1 for mAb 3A11 staining). Open histogram represents CD318 (Panel A) or mAb 3A11 (Panel B) staining.
Figure 2:
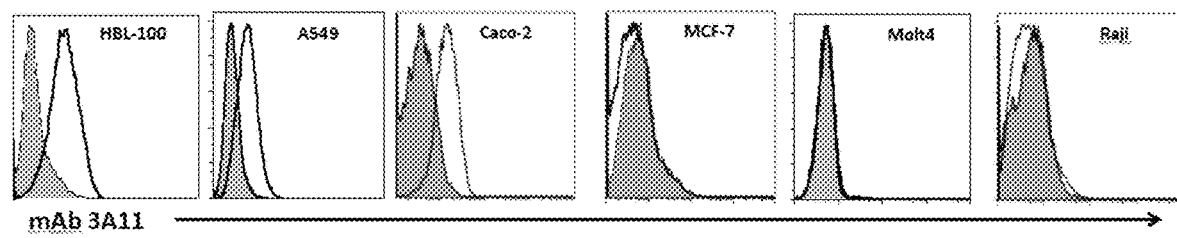

Flow Cytometric Analysis of Cells Normally Expressing or not Expressing CD318 Using Both mAb 3A11 and a Commercial Anti-CD318 mAb CD318 has been reported to be present on A549(14), HBL-100(28) and Caco2(29) cells, but not on MCF-7(30), Molt-4(31) or Raji cells (14). We analyzed all of these cells with a commercial anti-CD318 mAb (FIG. 2A) or mAb 3A11 (FIG. 2 Panel B), and found exactly the same staining pattern, suggesting that mAb 3A11 and the anti-CD318 mAb recognize the same antigen.

Figure 3:
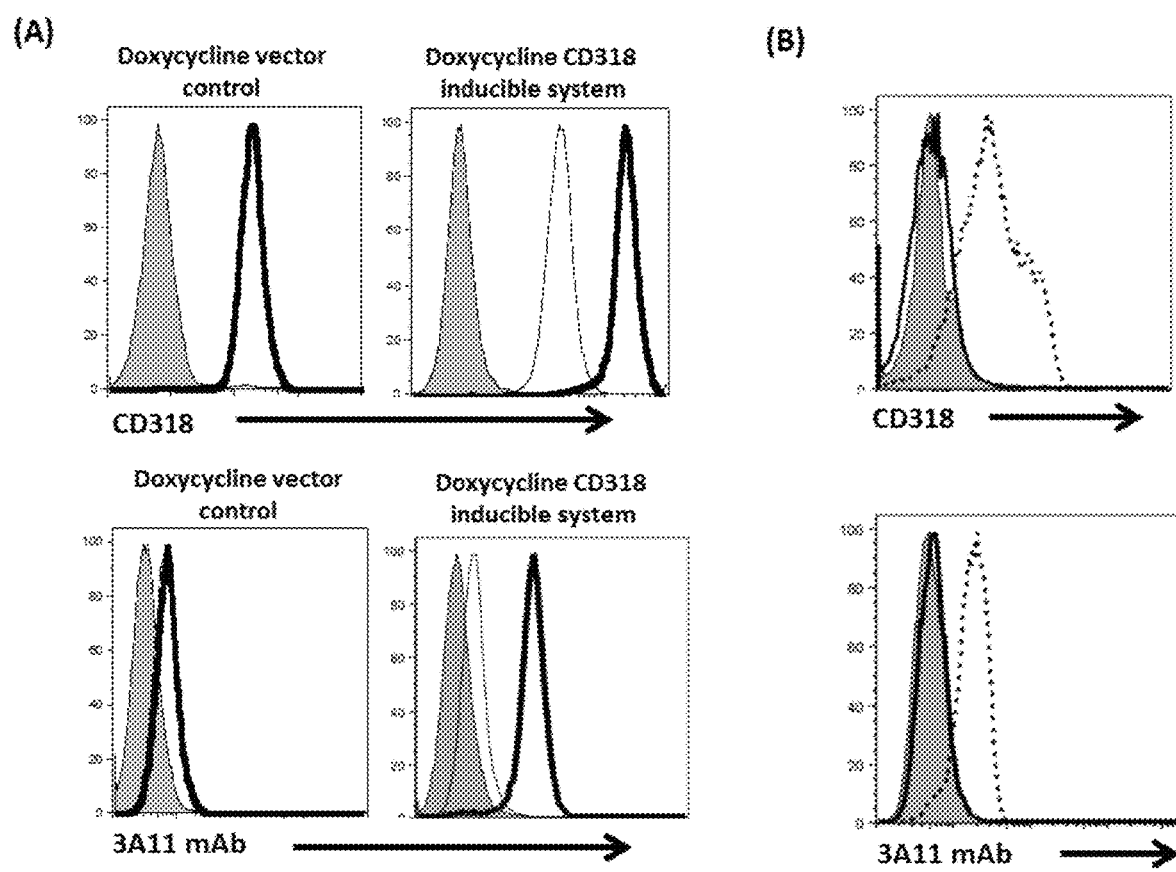
FIGS. 3A-3B The anti-CD318 mAb and mAb 3A11 have an identical staining pattern on cells engineered to upregulate or downregulate CD318 expression. (Panel A) The anti-CD318 mAb and mAb 3A11 staining on cells overexpressing CD318. MDA-468 cells transfected with vector alone (control) or a doxycycline-inducible CD318 expressing construct were incubated with doxycycline overnight, then stained either with CD318 Ab (Panel A, upper panels) or mAb 3A11 (Panel A, lower panels) and analyzed by flow cytometry. Shaded histograms: isotype controls, Thin open histograms: basal expression level of anti-CD318 mAb/mAb 3A11 staining before doxycycline induction, Thick open histograms: level of anti-CD318 mAb/mAb 3A11 staining after doxycycline induction. Data are representative of 3 independent experiments. (Panel B) The anti-CD318 mAb and mAb 3A11 staining on cells with CD318 knocked down. MDA-468 WT and CD318 Knockdown cells were stained with either anti-CD318 mAb (Panel B, upper panel) or mAb 3A11 (Panel B, lower panel) and analyzed by flow cytometry. Thin lines: isotype controls, dashed lines: WT cells stained with the anti-CD318 mAb or mAb 3A11. Thick lines, CD318 knocked down cells stained with the anti-CD318 mAb and mAb 3A11. Data are representative of 3 independent experiments.

Flow Cytometric Analysis of Engineered Cells with CD318 Overexpression or Downregulation We cannot exclude the slight possibility in the above-described flow cytometry experiments that it was a coincidence that mAb 3A11 and the anti-CD318 mAb might recognize different antigens that happen to have the same expression pattern on the various examined cell lines. To address this issue, we studied the transfected MDA-468 cells that overexpress CD318 after doxycycline induction (13, 32) and the transfected MDA-468 cells knocked down for CD318 expression using shRNA (32) by flow cytometry using the commercial anti-CD318 mAb and mAb 3A11. We found that, consistent with previous reports (32), following doxycycline treatment the expression of CD318 increases above basal levels in MDA-468 expressing CD318 inducible system and not in cells expressing empty vector (control) (FIG. 3A). These assays also showed that staining of these cells expressing CD318 with mAb 3A11 resulted in exactly the same pattern as the anti-CD318 mAb (FIG. 3A), while, in CD318 knocked down MDA-468 cells, which are CD318-negative, staining with either anti-CD318 mAb or mAb 3A11 was also negative (FIG. 4B). These additional data confirmed that mAb 3A11 recognizes CD318.

CD6 Binding Analysis on Cells Expressing Both CD166 and CD318, or CD318 Alone

Figure 4:
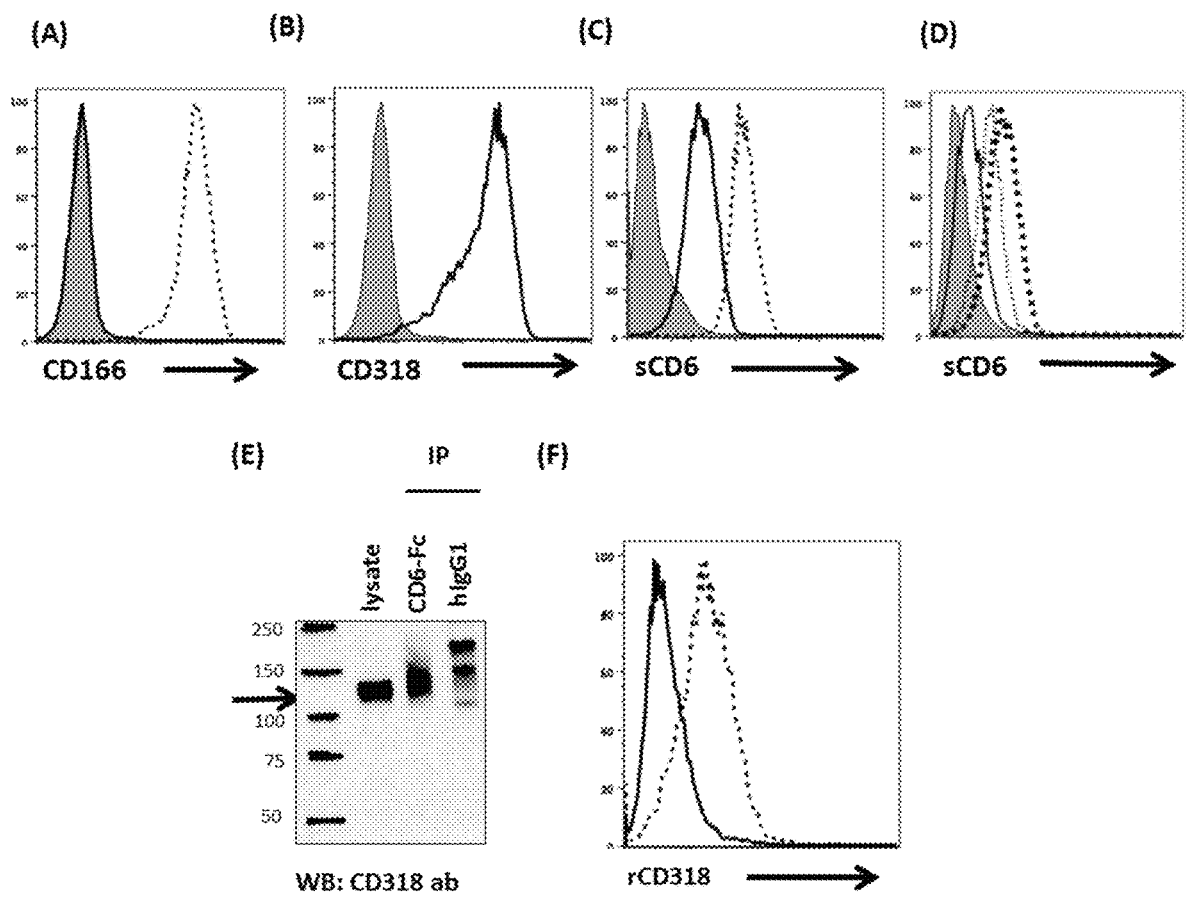
FIGS. 4A-4F CD6 interacts with CD318. (Panel A) HT1080 CD166 KO cells are deficient of CD166. The CD166 KO cells were analyzed for CD166 expression by flow cytometry. Thin line, isotype control, Thick line, CD166 KO cells stained with an anti-CD166 mAb. Thin dash line, WT HT1080 cells stained with the anti-CD166 mAb. Data are representative of 5 independent experiments. (Panel B) HT1080 CD166 KO cells express CD318. The CD166 KO cells were analyzed for CD318 expression by flow cytometry using the anti-CD318 mAb. Thin line, isotype control, Thick line, CD166 KO cells stained with the anti-CD318 mAb. Data are representative of 5 independent experiments. (Panel C) CD6 binds to WT and CD166 KO cells. WT and CD166 KO cells were incubated with the same concentrations of human IgG1 (control) or recombinant human CD6-Fc fusion protein (1 µM), followed by detecting the cell surface-bound CD6 using an Alexa488-anti-human IgG Ab. Thin line, isotype control; Thick line, CD166 KO cells stained with CD6; and Thin dash line, WT cells stained with CD6. Data are representative of 6 experiments. (Panel D) Binding of CD6 onto CD166 KO cells is competitively inhibited by soluble CD318. CD166 KO cells were incubated with recombinant human CD6-Fc fusion protein (1 µM) in the presence of different concentrations of recombinant soluble CD318 (0, 1 and 3 µM) then level of cell surface bound CD6 were quantitated by flow cytometric analysis after staining the cells with an Alexa488-anti-human IgG Ab. Thin shaded line: isotype control; Thick dash line, no rCD318; thin dash line, 1 µM CD318, thin line 3 µM rCD318. The numbers in parenthesis represent the molar concentrations of either rHCD6 or rCD318. Data are representative of 6 independent experiments. (Panel E) CD6 immunoprecipitates CD318 from the CD166 KO cell lysates. CD166 KO cell lysates were immunoprecipitated with the same concentrations of either soluble CD6 or human IgG1, then the immunoprecipitates were separated by SDS-PAGE and probed with the anti-CD318 Ab, showing that CD6 selectively pulled down CD318 (arrow). Data are representative of 8 independent experiments. (Panel F) Soluble CD318 binds to CHO cells that express CD6 on the surface. Control CHO cells (solid line) and CHO cells expressing human CD6 (dotted line) were incubated with recombinant CD318. After washing, the binding of CD318 on the cell surface was assessed by flow cytometry after staining the cells with the anti-CD318 mAb.

After confirming that CD318 is the protein recognized by mAb 3A11 in the above experiments, we tested whether CD318 indeed binds to CD6, as suggested by previous studies. We have already shown that soluble CD6 protein can be used to stain cells expressing CD6 ligands in flow cytometric assays. The human fibrosarcoma cell line HT-1080 expresses both CD318 and CD166(33, 34), and we generated an HT-1080 CD166 KO cell line by CRISPR/Cas9 technology to exclude the previously known CD6-CD166 interaction (FIG. 4A). We first confirmed that indeed our HT-1080 CD166 KO cell line expresses CD318 but not CD166 (FIG. 4B), then stained the WT and CD166 KO cells with the soluble CD6 protein. We found that, in the absence of CD166, the binding of CD6 to the surface of these cells was significantly reduced but still evident (FIG. 4C), further evidence that CD6 has ligand(s) other than CD166. We then carried out a competitive binding assay using our prepared soluble rCD318 protein and found that binding of CD6 to the CD166 KO cells was reduced by rCD318 in a dose-dependent manner (FIG. 4D). In addition, we incubated soluble CD6-Fc protein or the same amount of purified human IgG1 with the CD166 KO cell lysates, and probed the CD6-participated proteins with a commercial anti-CD318 antibody in Western Blot. We found that CD6-Fc protein, but not the control human IgG1 protein, pulled down a protein that recognized by the anti-CD318 antibody (FIG. 4 Panel E). Finally, we stained transfected CHO cells expressing human CD6 on the surface and control CHO cells with the soluble rCD318 and found that rCD318 binds to human CD6-expressing CHO cells but not the control CHO cells (FIG. 4F). These results demonstrate that CD6 binds to CD318.

CD318 KO Mice are Protected in EAE

Figure 5:
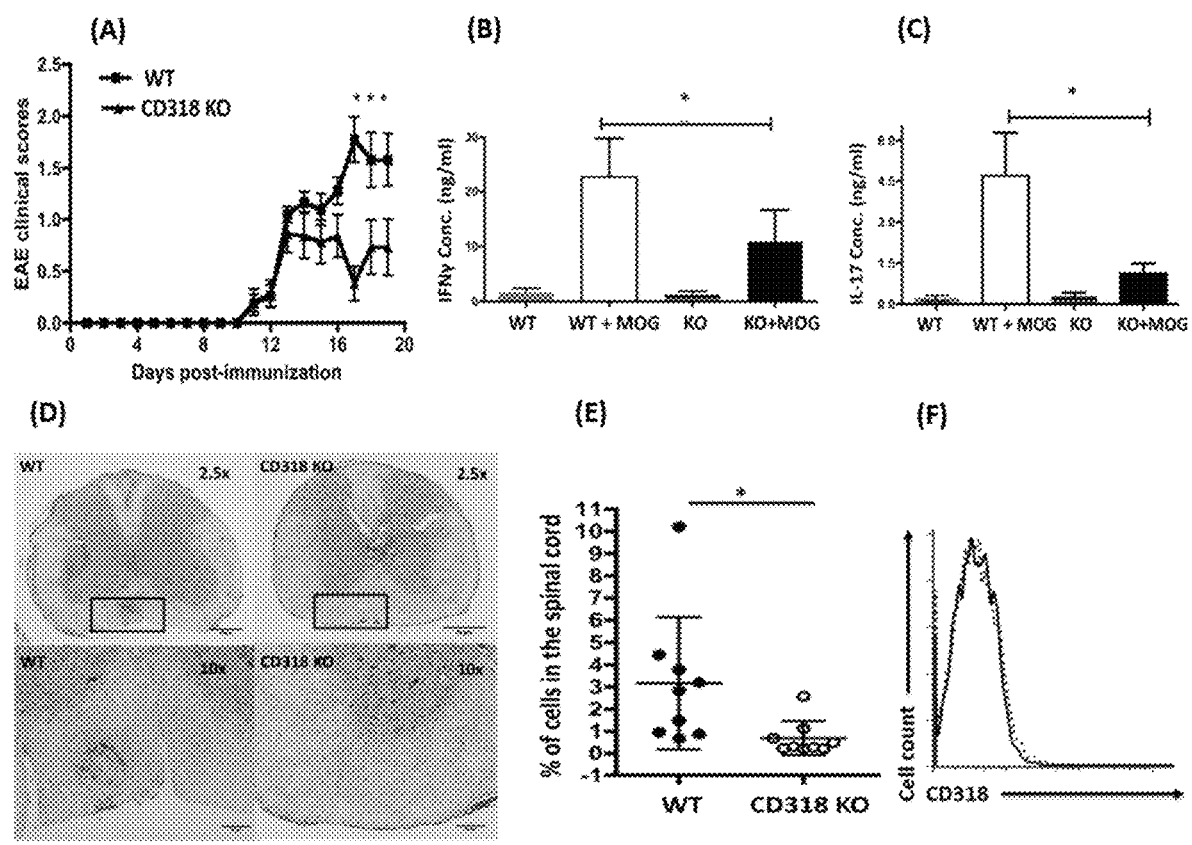
FIGS. 5A-5F CD318 KO mice are protected in EAE. (Panel A) WT and CD318 KO mice were immunized with $MOG_{35-55}$ to induce EAE and the development of EAE was monitored daily by clinical scoring. Combined results from 5 individual experiments. WT n=21, CD318 KO n=25, data are mean±SEM, *p<0.05, (Panel B) and (Panel C). At the end of the experiments, splenocytes were collected and incubated with or without 10 µg/ml of $MOG_{35-55}$ peptide for 72 hr. Levels of IFNγ(B) and IL-17 (Panel C) in the culture supernatants were measured by respective ELISA. Combined results from 3 individual experiments, WT n=17, CD318 KO n=16, data are mean±SEM, * p<0.05; (Panel D) representative histology images of spinal cord sections from WT (Panel D, left panels) and CD318 KO (Panel D, right panels) mice in EAE, showing significantly reduced inflammation in the CD318 KO mouse spinal cords. Spinal cords were collected at the end of the experiment and processed for H&E staining. Squares in the upper panels show the areas that were amplified in the lower panels (Panel E). Flow cytometric analysis of infiltrated CD4+ T cells in spinal cord from WT and CD318 KO mice in EAE, showing significantly reduced CD4+ T cell infiltration in the spinal cords of the CD318 KO mice in EAE. Spinal cords were collected at the end of the experiment, minced and digested with collagenase. Single cell suspension was prepared after Percoll centrifugation, stained with an anti-mouse CD4 mAb, and analyzed by a flow cytometer. (Panel F). Mouse BMECs do not constitutively express CD318. Primary BMECs were isolated from WT mice, characterized and stained with sheep anti-mouse CD318 IgG (solid line) or control IgG (dotted line), then analyzed on a flow cytometer.

Even though the potential role of CD318 in immune regulation has never been studied, our new data showing that it is a ligand for CD6, a molecule that is important in the pathogenesis of EAE and MS (35) suggests that it might have a previously unknown immunoregulatory role and might regulate the development of EAE/MS. To test this, we induced EAE in matched WT and CD318 KO mice by immunizing them with $MOG_{35-55}$ peptide in CFA plus pertussis toxin and found that, like CD6 KO mice (35), CD318 KO mice had attenuated disease severity in EAE (FIG. 5 Panel A). These CD318 KO mice in EAE showed reduced MOG-specific Th1 (FIG. 5 Panel B) and Th17 (FIG. 5 Panel C) responses and had significantly decreased inflammation (FIG. 5 Panel D) and CD4+ T cell infiltration (FIG. 5 Panel E) in the spinal cord. These results reveal a previously unknown role for CD318 in immune regulation, providing further evidence that it is important for CD6 function in EAE.

Figure 6:
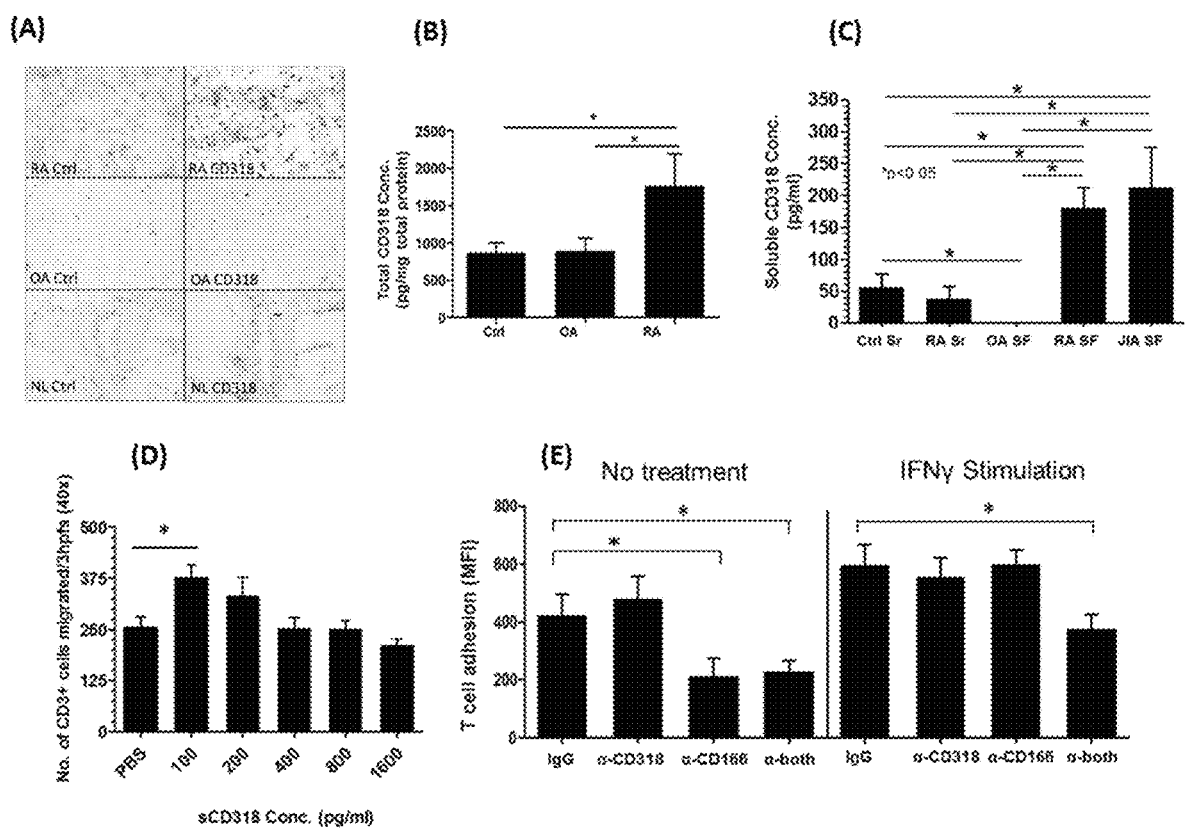
FIGS. 6A-6E CD318 is a biomarker for inflammatory arthritis and chemotactic for T cells. (Panel A) CD318 is highly expressed in synovial tissues from RA patients. Synovial tissue sections from RA, OA and non-relevant controls (NL) were stained with either mAb 3A11 (mouse anti-human CD318) or the same amount of control IgGs, then slides were examined under a microscope. (Panel B) Levels of total CD318 are elevated in synovial tissues from RA patients. Synovial tissue from patients with RA (n=13), OA (n=20) and normal synovial tissues (Ctrl, n=17) were homogenized and levels of total CD318 were analyzed by ELISA. (Panel C) Levels of soluble CD318 are significantly higher in synovial fluids from patients with RA (n=36), JIA (n=10) than those from patients with OA (n=28). Sr: serum and SF: synovial fluid. (Panel D) Soluble CD318 is chemotactic to T cells. T cell migration towards vary concentrations of CD318 (100, 200, 400, 800, and 1600 pg/ml) were assessed in Boyden chemotaxis chamber. PBS, negative control. Readings represent the number of cells migrating through the membrane (the sum of three high power 40× fields/well, averaged for each quadruplicate well). (E Panel) T cell adhesion to IFNγ stimulated synovial fibroblasts in the presence of mouse IgG (control), anti-CD318, anti-CD166 or both were measured by a synergy plate reader.

Measurement of CD318 Levels in Synovial Tissues from RA and OA Patients by ELISA We have established previously that the antigen recognized by the mAb 3A11 (now shown to be CD318) is highly expressed in synovial fibroblasts from RA patients after IFNγ stimulation. To explore a potential role for CD318 in the pathogenesis of arthritis, we first carried out IHC staining for CD318 in synovial tissue sections of RA, OA and non-relevant controls. We found that CD318 is highly expressed only in RA synovial tissues (FIG. 6 Panel A). We then homogenized synovial tissues from patients without or with RA or OA and measured levels of total CD318 in them by ELISA. We found that CD318 was detectable in synovial tissues from all the synovial tissues examined. While levels of CD318 were comparable between the control groups without arthritis and with OA, levels of CD318 in synovial tissues from RA patients were significantly elevated (FIG. 6 Panel B).

Measurement of Soluble CD318 Levels in Sera and Synovial Fluids from RA and OA Patients by ELISA Soluble CD318 has been found in cancer cell culture supernatants and in urine samples from men with high-risk prostate cancer (13). We first measured levels of soluble CD318 in sera from RA patients and healthy donors. We found that levels of soluble CD318 in the sera were very low, barely above the sensitivity of the ELISA assay that we used (FIG. 6 Panel C). We also examined synovial fluids from patients with RA, JIA and OA by the same ELISA, and found that levels of soluble CD318 were significantly higher in synovial fluids than in plasma, and that levels of soluble CD318 were significantly higher in synovial fluids from both RA and JIA patients than in those from the OA patients (CD318 was not detectable in synovial fluids from OA patients) (FIG. 6 Panel C). These data suggest that soluble CD318 is produced within the joints and that it could be used a novel biomarker in synovial fluids to distinguish OA from RA and JIA.

T Cell Chemotaxis in Response to Soluble CD318

The gradient between serum and synovial fluid levels of soluble CD318 and the elevated levels of CD318 in synovial fluids from patients with RA and JIA but not in OA led us to assess the possibility that soluble CD318 might be chemotactic for T lymphocytes. Using a modified Boyden chamber assay we found that indeed, at a concentration that approximated the difference between the mean RA serum and RA synovial fluid soluble CD318 levels, peripheral blood T cells migrated in response to soluble CD318 as a single stimulus (Fig. Panel Contributions of CD6 Ligands to Adhesion Between T Cells and Synovial Fibroblasts Previous work has suggested that a CD6 ligand other than CD166 could contribute to adhesion between human T lymphocytes and various IFNγ-treated non-hematopoietic cell types (10, 11, 36). To evaluate the roles of CD166 and CD318 in interactions between T cells and synovial fibroblasts, we performed adhesion assays using fluorescently tagged T cells and synovial fibroblasts that were or were not pre-cultured with IFNγ. In these assays, we found that CD6 ligands were significantly involved in the adhesion of T cells to synovial fibroblasts (FIG. 6 Panel E). Without IFNγ pre-treatment of the synovial fibroblasts, only CD166 was functionally important in these adhesion assays, consistent with the minimal expression of CD318 on these cells. Interestingly, when IFNγ-treated synovial fibroblasts were used, both ligands were functional, and adhesion was substantially interrupted only when both were simultaneously masked with monoclonal antibodies. These results are consistent with important functional roles for both CD6 ligands in synovial tissue in vivo.

In this Example, using MS analysis, we identified abundant CD318-derived peptides in mAb 3A11-immunoprecipitated proteins. CD318 also met the previously published criteria of a 3A11 antigen, suggesting that CD318 is the antigen recognized by mAb 3A11. We confirmed the MS results by probing the mAb 3A11-immunoprecipitated proteins with a commercial anti-CD318 antibody, and by producing and probing recombinant CD318 with mAb 3A11 in western blots. In addition, we found that mAb 3A11 and the established CD318 mAb have the same staining patterns on cells known to naturally express or lack CD318, and on cells engineered to overexpress or knockdown CD318 expression. Using soluble CD6, soluble CD318, cells that express both CD166 and CD318 or CD318 alone, and transfected CHO cells expressing CD6 in flow cytometric analyses and pull-down experiments, we confirmed that CD318 does bind to CD6. Finally, we found that CD318 is abundant in synovial tissues and while levels of total CD318 are similar in synovial tissues from controls and OA patients, they are significantly elevated in RA patients. Moreover, a soluble form of CD318 can be readily detected in synovial fluids from patients with inflammatory (RA, JIA) but not non-inflammatory (OA) arthritis, and these levels are appreciably higher than those in the serum. Of particular interest, both the membrane-bound and soluble forms of CD318 are functionally active in vitro, in adhesion and chemotaxis assays, respectively, that are arguably relevant to components of the pathogenesis on joint inflammation in vivo.

The distinct patterns of expression of CD318 compared to CD166 are striking—while CD166 is expressed widely on a broad range of hematopoietic and non-hematopoietic cells, including activated T lymphocytes, CD318 expression appears to be confined to non-hematopoietic lineages, such as fibroblasts, keratinocytes, epithelial cells and a variety of neoplastic cells (10, 11, 34, 36). The one possible exception to the lack of CD318 expression on hematopoietic cells is a subset of cord blood hematopoietic progenitors (37). Thus, engagement of CD6 by CD318 is an unusual example of a ligand-receptor interaction between a lymphocyte-specific cell surface glycoprotein that can participate in T cell activation (CD6) and a molecule (CD318) that is found only on cells that are traditionally considered not to be components of the immune system. This interaction points to an ability of T cells to specifically receive and recognize distinct signals from "non-immune system" tissue cells that may be important in organ-targeted autoimmune diseases, such as synovial fibroblasts and keratinocytes.

Membrane-anchored CD318 appears to be a mediator of T cell adhesion to tissue cells, such as synovial cells and keratinocytes, and our data suggest that under some conditions both CD6 ligands, CD166 and CD318, can cooperatively participate in adhesion to T cells. These two CD6 ligands appear to recognize distinct epitopes of CD6, raising the possibility that CD6 can be engaged simultaneously by both of its ligands to form a tri-molecular complex. Structural demonstration of such a complex during interactions between intact cells is an important goal for future experiments. Early studies of CD6 identified distinct immunologic epitopes that appeared to mediate different functional effects on T cells (38), and more recent work has localized the binding domains on CD6 and CD166 that are involved in the CD6/CD166 interaction (39). CD6 was identified as a risk gene for MS (2-5) and we recently showed that CD6 KO mice are protected from EAE and that treating mice with an anti-CD6 mAb ameliorates CNS injury in EAE (35), suggesting that CD6 could be a new target for treating MS. Interestingly, although treating WT mice with a mAb against CD166, the first identified ligand of CD6, ameliorates EAE (40), CD166 KO mice show exacerbated EAE potentially due to reduced expression of blood-brain barrier (BBB) junctional proteins, leading to increased permeability of CNS blood vessels in the CD166 KO mice (41). Different from the CD166 KO mice, we found that CD318 KO mice were protected in EAE, in association with reduced MOG-specific T cell responses and decreased CNS T-cell infiltration, suggesting that CD318 is an important ligand for CD6. We also isolated primary brain microvascular endothelial cells (BMECs) from WT mice and examined CD318 expression on this critical component of the BBB by flow cytometry. We found that in contrast to CD166, which is highly expressed on the mouse BMECs (40, 41), CD318 is not constitutively expressed on these cells at all (FIG. 5 Panel F).

The signal transduction pathways that are activated by CD318 binding to CD6, with or without concurrent binding of CD166 to CD6, remain to be elucidated, both downstream of CD6 in the T lymphocyte and downstream of CD318 and CD166 in non-T cells that express these ligands. Signal transduction events in synovial fibroblasts generated by cell-cell adhesion events that involve CD6 and CD318 are likely to be distinct from pathways activated by anti-adhesive effects of the intracellular domain of CD318 that have been described in cancer cells (42). In cancer cells CD318 is phosphorylated and can enhance downstream phosphorylation events, in part linked to signaling through the epidermal growth factor receptor (43, 44). Moreover, cleavage of full-length 135 kD CD318 by serine proteases creates a smaller membrane-retained 70 kD form that either associates with membrane integrins or homodimerizes, and generates downstream signaling events that enhance cancer cell invasiveness and metastasis (16, 44). Cleavage of CD318 can be blocked by dexamethasone (45). Like cancer cells, RA synovial fibroblasts are locally invasive and are stimulated by a variety of growth factors. Moreover, intra-articular injection of corticosteroid ameliorates joint inflammation. It will be important to elucidate the potential roles of CD318 in migration and invasion of synovial fibroblasts, and to assess the effect of engagement of CD318 by CD6 on these processes.

On synovial fibroblasts and keratinocytes CD318 is upregulated by IFNγ. However, on cancer cells its expression is increased following engagement of the epidermal growth factor (EGF) receptor by EGF (46). In cancer CD318 is also upregulated by hypoxia-inducible factor 2alpha, which is also potentially relevant to CD318 expression on synovial fibroblasts since inflamed synovium is a hypoxic environment. Methylation of sites near CD318 has been proposed as a critical element of epigenetic control of its expression. In bone marrow stromal cells reciprocal CD146+CD318− and CD146−CD318+ subsets of marrow fibroblasts have been identified that have distinct patterns of gene expression (47); whether this is also true in synovium or other tissues is as yet unknown.

The elevated levels of soluble CD318 in inflamed synovial tissue and fluid (RA and JIA) raise questions regarding its function, and identify this molecule as a measurable biomarker. Our data indicate that soluble CD318 is chemotactic for T cells, which are not present in normal synovial tissue, but which accumulate in large numbers in RA and JIA synovium through mechanisms that are as yet not fully defined. Importantly, the concentration at which soluble CD318 is chemotactic corresponds to the in vivo concentration gradient between RA serum and RA synovial fluid, indicating that this in vitro assay is likely to be physiologically relevant. Whether soluble CD318 is derived by protease-mediated shedding from the synovial fibroblast surface or by secretion of soluble CD318 from the synovial fibroblasts is as yet unknown. The chemotactic effects of soluble CD318 resemble in some respects resemble chemotactic properties of CD13, another membrane protein on synovial fibroblasts that also is present at high concentrations as a soluble molecule in inflammatory joint fluid (48). Neither CD13 nor CD318 show structural resemblance to conventional chemokines, but there is evidence that CD13, like classical chemokines, signals through a G-protein coupled receptor (48).

Although biologic therapeutics have led to important improvements in the treatment of RA and JIA, these agents impair host defenses to various pathogens and do not selectively target molecular interactions that are more important in pathogenic autoimmunity compared to normal immune responses. Identification of CD318 as a ligand of CD6 creates a therapeutic target at the level of the T cell/synovial fibroblast interaction that is not relevant to T cell interactions with professional antigen-presenting cells in lymphoid organs.

REFERENCES

1. Pinto M, and Carmo A M. CD6 as a therapeutic target in autoimmune diseases: successes and challenges. BioDrugs: clinical immunotherapeutics, biopharmaceuticals and gene therapy. 2013; 27(3):191-202.
2. International Multiple Sclerosis Genetics C. The genetic association of variants in CD6, TNFRSF1A and IRF8 to multiple sclerosis: a multicenter case-control study. PLoS One. 2011; 6(4):e18813.
3. Swaminathan et al. Validation of the CD6 and TNFRSF1A loci as risk factors for multiple sclerosis in Spain. J Neuroimmunol. 2010; 223(1-2): 100-3.
4. De Jager et al. Meta-analysis of genome scans and replication identify CD6, IRF8 and TNFRSF1A as new multiple sclerosis susceptibility loci. Nat Genet. 2009; 41(7):776-82.
5. Heap et al. Genome-wide analysis of allelic expression imbalance in human primary cells by high-throughput transcriptome resequencing. Hum Mol Genet. 2010; 19(1): 122-34.
6. Aruffo et al., The lymphocyte glycoprotein CD6 contains a repeated domain structure characteristic of a new family of cell surface and secreted proteins. J Exp Med. 1991; 174(4):949-52.
7. Bowen et al. Cloning, mapping, and characterization of activated leukocyte-cell adhesion molecule (ALCAM), a CD6 ligand. J Exp Med. 1995; 181(6):2213-20.
8. Zimmerman et al., Long-term engagement of CD6 and ALCAM is essential for T-cell proliferation induced by dendritic cells. Blood. 2006; 107(8):3212-20.
9. Nair et al., CD6 synergistic co-stimulation promoting proinflammatory response is modulated without interfering with the activated leucocyte cell adhesion molecule interaction. Clin Exp Immunol. 2010; 162(1):116-30.
10. Joo et al., Evidence for the expression of a second CD6 ligand by synovial fibroblasts. Arthritis Rheum. 2000; 43(2):329-35.
11. Saifullah et al., Expression and characterization of a novel CD6 ligand in cells derived from joint and epithelial tissues. J Immunol. 2004; 173(10):6125-33.
12. Alonso-Ramirez et al., Rationale for Targeting CD6 as a Treatment for Autoimmune Diseases. Arthritis. 2010; 2010(130646.
13. Bhatt et al., Adhesion signaling by a novel mitotic substrate of src kinases. Oncogene. 2005; 24(34):5333-43.
14. Scherl-Mostageer et al., Identification of a novel gene, CDCP1, overexpressed in human colorectal cancer. Oncogene. 2001; 20(32):4402-8.
15. Hooper et al., Subtractive immunization using highly metastatic human tumor cells identifies SIMA135/CDCP1, a 135 kDa cell surface phosphorylated glycoprotein antigen. Oncogene. 2003; 22(12):1783-94.
16. Casar et al., In vivo cleaved CDCP1 promotes early tumor dissemination via complexing with activated beta1 integrin and induction of FAK/PI3K/Akt motility signaling. Oncogene. 2014; 33(2):255-68.
17. Spassov et al., The transmembrane src substrate Trask is an epithelial protein that signals during anchorage deprivation. The American journal of pathology. 2009; 174(5): 1756-65.
18. Conze et al., CDCP1 is a novel marker for hematopoietic stem cells. Annals of the New York Academy of Sciences. 2003; 996(222-6).
19. Buhring et al., CDCP1 identifies a broad spectrum of normal and malignant stem/progenitor cell subsets of hematopoietic and nonhematopoietic origin. Stem cells. 2004; 22(3):334-43.
20. Uekita T, and Sakai R. Roles of CUB domain-containing protein 1 signaling in cancer invasion and metastasis. Cancer science. 2011; 102(11):1943-8.
21. Perry et al., Expression of the CUB domain containing protein 1 (CDCP1) gene in colorectal tumour cells. FEBS letters. 2007; 581(6):1137-42.
22. Uekita et al., CUB-domain-containing protein 1 regulates peritoneal dissemination of gastric scirrhous carcinoma. The American journal of pathology. 2008; 172(6): 1729-39.
23. Awakura et al., Microarray-based identification of CUB-domain containing protein 1 as a potential prognostic marker in conventional renal cell carcinoma. Journal of cancer research and clinical oncology. 2008; 134(12): 1363-9.

24. Razorenova et al., VHL loss in renal cell carcinoma leads to up-regulation of CUB domain-containing protein 1 to stimulate PKC{delta}-driven migration. Proc Natl Acad Sci USA. 2011; 108(5):1931-6.

25. Wong et al., Phosphorylation of the SRC epithelial substrate Trask is tightly regulated in normal epithelia but widespread in many human epithelial cancers. Clinical cancer research: an official journal of the American Association for Cancer Research. 2009; 15(7):2311-22.

26. Spassov et al., Trask loss enhances tumorigenic growth by liberating integrin signaling and growth factor receptor cross-talk in unanchored cells. Cancer research. 2013; 73(3): 1168-79.

27. Jayaraman, Biocon's first-in-class anti-CD6 mAb reaches the market. Nature biotechnology. 2013; 31(12): 1062-3.

28. Seidel et al., Evaluation of CUB-Domain-Containing Protein (CDCP1)-Expression as Predictive Marker of Adhesion-Independant Cell Survival in Breast Cancer Cell Lines. Cancer research. 2009; 69(24):878s-s.

29. Wortmann et al., Cellular settings mediating Src Substrate switching between focal adhesion kinase tyrosine 861 and CUB-domain-containing protein 1 (CDCP1) tyrosine 734. J Biol Chem. 2011; 286(49):42303-15.

30. Kollmorgen et al., Antibody mediated CDCP1 degradation as mode of action for cancer targeted therapy. Mol Oncol. 2013; 7(6):1142-51.

31. Ikeda et al. Epigenetic regulation of the expression of the novel stem cell marker CDCP1 in cancer cells. J Pathol. 2006; 210(1):75-84.

32. Spassov et al., Phosphorylation of Trask by Src kinases inhibits integrin clustering and functions in exclusion with focal adhesion signaling. Molecular and cellular biology. 2011; 31(4):766-82.

33. Lunter et al., Activated leukocyte cell adhesion molecule (ALCAM/CD166/MEMD), a novel actor in invasive growth, controls matrix metalloproteinase activity. Cancer research. 2005; 65(19):8801-8.

34. Miyazawa et al., CUB domain-containing protein 1, a prognostic factor for human pancreatic cancers, promotes cell migration and extracellular matrix degradation. Cancer research. 2010; 70(12):5136-46.

35. Li et al., CD6 as a potential target for treating multiple sclerosis. Proc Natl Acad Sci USA 2017; in press 36. Singer et al., CD6 dependent interactions of T cells and keratinocytes: functional evidence for a second CD6 ligand on gamma-interferon activated keratinocytes. Immunology letters. 1997; 58(1):9-14.

37. Takeda et al., CD318/CUB-domain-containing protein 1 expression on cord blood hematopoietic progenitors. Experimental and therapeutic medicine. 2010; 1(3):497-501.

38. Bott et al., Activation of human T cells through CD6: functional effects of a novel anti-CD6 monoclonal antibody and definition of four epitopes of the CD6 glycoprotein. Int Immunol. 1993; 5(7):783-92.

39. Chappell et al., Structures of CD6 and Its Ligand CD166 Give Insight into Their Interaction. Structure. 2015; 23(8):1426-36.

40. Cayrol et al. Activated leukocyte cell adhesion molecule promotes leukocyte trafficking into the central nervous system. Nature immunology. 2008; 9(2):137-45.

41. Lecuyer et al. Dual role of ALCAM in neuroinflammation and blood-brain barrier homeostasis. Proc Natl Acad Sci USA. 2017.

42. Spassov et al., The structural features of Trask that mediate its anti-adhesive functions. PLoS One. 2011; 6(4):e19154.

43. He et al., New crossroads for potential therapeutic intervention in cancer—intersections between CDCP1, EGFR family members and downstream signaling pathways. Oncoscience. 2016; 3(1):5-8.

44. Wright et al., CDCP1 cleavage is necessary for homodimerization-induced migration of triple-negative breast cancer. Oncogene. 2016.

45. Law et al. Glucocorticoids and histone deacetylase inhibitors cooperate to block the invasiveness of basal-like breast cancer cells through novel mechanisms. Oncogene. 2013; 32(10):1316-29.

46. Dong et al., The cell surface glycoprotein CUB domain-containing protein 1 (CDCP1) contributes to epidermal growth factor receptor-mediated cell migration. J Biol Chem. 2012; 287(13):9792-803.

47. Iwata et al., CDCP1 identifies a CD146 negative subset of marrow fibroblasts involved with cytokine production. PLoS One. 2014; 9(10):e109304.

48. Morgan et al. Expression and function of aminopeptidase N/CD13 produced by fibroblast-like synoviocytes in rheumatoid arthritis: role of CD13 in chemotaxis of cytokine-activated T cells independent of enzymatic activity. Arthritis Rheumatol. 2015; 67(1):74-85.

49. He et al. Elevated CDCP1 predicts poor patient outcome and mediates ovarian clear cell carcinoma by promoting tumor spheroid formation, cell migration and chemoresistance. Oncogene. 2016; 35(4):468-78.

50. Wortmann et al., The cell surface glycoprotein CDCP1 in cancer—insights, opportunities, and challenges. IUBMB Life. 2009; 61(7):723-30.

51. Li et al., Augmenting DAF levels in vivo ameliorates experimental autoimmune encephalomyelitis. Molecular immunology. 2009; 46(15):2885-91.

52. Abdul-Majid et al., Screening of several H-2 congenic mouse strains identified H-2(q) mice as highly susceptible to MOG-induced EAE with minimal adjuvant requirement. Journal of neuroimmunology. 2000; 111(1-2):23-33.

All publications and patents mentioned in the specification and/or listed below are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope described herein

We claim:

1. A method of performing an activity based on a level of CD318 protein or mRNA in a sample from a human subject comprising:
   a) determining protein and/or mRNA expression level of CD318 in a sample from a human subject, with, or suspected of having, an autoimmune disease; and
   b) identifying increased protein and/or mRNA expression levels of CD318 in said sample, and treating said subject with a therapeutic agent used to treat an autoimmune disease;
   wherein said autoimmune disease is rheumatoid arthritis, juvenile inflammatory arthritis, or multiple sclerosis, and
   wherein said therapeutic agent comprises an anti-CD318 antibody or antigen binding fragment thereof, or an anti-CD318 siRNA.

2. The method of claim 1, wherein said sample is selected from the group consisting of: a plasma sample, a serum sample, synovial fluid sample, and synovial tissue sample.

3. The method of claim 1, wherein said determining comprises contacting said sample with an anti-CD318 antibody.

4. A method of treatment comprising:
   a) identifying a human subject as having increased expression levels of CD318 protein and/or mRNA, wherein said subject has, or is suspected of having, rheumatoid arthritis, juvenile inflammatory arthritis, or multiple sclerosis, and
   b) treating said subject with a therapeutic agent, wherein said therapeutic agent is an anti-CD318 antibody or antigen binding fragment thereof, or an anti-CD318 siRNA.

5. The method of claim 4, wherein said identifying comprises receiving a report that said subject has increased expression levels of CD318 protein and/or mRNA.

* * * * *